United States Patent [19]

Kuhla et al.

[11] Patent Number: 4,543,352
[45] Date of Patent: Sep. 24, 1985

[54] NAPHTHALENE AMINOALKYLENE ETHERS AND THIOETHERS, AND THEIR PHARMACEUTICAL USES

[75] Inventors: Donald E. Kuhla, Doylestown; Henry F. Campbell, Lansdale; William L. Studt, Harleysville, all of Pa.

[73] Assignee: William H. Rorer, Inc., Fort Washington, Pa.

[21] Appl. No.: 489,814

[22] Filed: Apr. 29, 1983

[51] Int. Cl.$^4$ .................. A61K 31/415; A61K 31/445; C07D 249/14; C07D 401/12

[52] U.S. Cl. .................. 514/212; 260/239 B; 260/245.5; 260/453.4; 260/465 E; 514/222; 514/232; 514/237; 514/272; 514/406; 514/427; 514/429; 514/523; 514/584; 514/600; 514/609; 514/634; 514/637; 514/362; 514/319; 514/326; 514/383; 514/399; 544/60; 544/132; 544/158; 544/162; 544/163; 544/166; 544/321; 546/208; 546/209; 546/230; 546/209; 546/230; 546/232; 548/135; 548/267; 548/346; 548/373; 548/563; 548/569; 548/577; 564/79; 564/103; 564/104; 564/243; 564/246; 564/346; 564/352

[58] Field of Search .................. 260/245.5; 548/267, 548/135; 564/352, 346, 79; 424/269, 246, 267, 248.52, 248.56; 544/60, 132; 546/208

[56] References Cited

U.S. PATENT DOCUMENTS

| 3,159,676 | 12/1964 | Spickett et al. | 564/352 |
| 3,504,092 | 3/1970 | Bencze | 564/352 |
| 3,634,507 | 1/1972 | Boissier et al. | 564/79 |
| 4,318,913 | 3/1982 | Clitherow et al. | 548/267 |
| 4,327,214 | 4/1982 | Rentzea et al. | 564/352 |
| 4,338,328 | 7/1982 | White | 548/267 |
| 4,374,248 | 2/1983 | Crenshaw et al. | 548/266 |
| 4,410,523 | 10/1983 | Ollis et al. | 548/267 |
| 4,442,110 | 4/1984 | Clitherow et al. | 548/267 |

FOREIGN PATENT DOCUMENTS 57564 8/1982 European Pat. Off. ............ 548/267

Primary Examiner—Alton D. Rollins
Attorney, Agent, or Firm—James A. Nicholson; Alexis Barron; Martin F. Savitzky

[57] ABSTRACT

A class of naphthalene aminoalkylene ether and thioether compounds exhibiting pharmacological activity including anti-secretory and anti-ulcerogenic activity, pharmaceutical compositions comprising these compounds, and methods for the treatment of gastrointestinal hyperacidity and ulcerogenic disorders in mammals using said compositions are disclosed.

5 Claims, No Drawings

NAPHTHALENE AMINOALKYLENE ETHERS AND THIOETHERS, AND THEIR PHARMACEUTICAL USES

FIELD OF THE INVENTION

This invention relates to a class of naphthalene compounds characterized by an ether or thioether substituent on one ring and an exocyclic nitrogen substituent on the other ring of the bicyclic naphthalene ring system and methods for the treatment of physiological disorders, including gastrointestinal disorders in humans and other mammals.

REPORTED DEVELOPMENTS

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid are implicated as causes of these disorders. Traditional treatment of these disorders has involved the administration of antacids to neutralize the excess gastric acid and the administration of antisecretory drugs which generally reduce the production of all gastric secretions.

In the last few years, the treatment of gastrointestinal disorders such as peptic ulcer has changed to include the use of anti-secretory drugs which selectively block the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_1$-receptor is involved in the bronchial and gastrointestinal smooth muscle stimulative action of histamine. Drugs which block this action are labelled "antihistamines" (e.g. mepyramine).

Black et al, cited above, described the group of substances which act at histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, and British published patent application GB No. 2067987A, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the active of strong gastric acid. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research*, Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl-carbamoylcarboxylic acids, esters and imides described in U.S. Pat. No. 4,321,372.

Compounds of the present invention comprise naphthalene ethers and thioethers which exhibit anti-secretory activity, $H_2$-receptor antagonist activity, anti-ulcer activity and cytoprotective activity.

SUMMARY OF THE INVENTION

This invention comprises a class of compounds according to Formula I

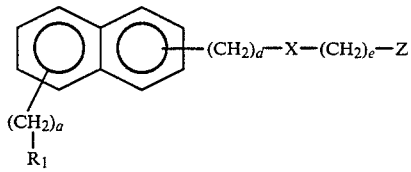

Formula I wherein:
a is 0, 1 or 2;
d is 0 or 1;
e is 2, 3 or 4;
X is oxygen, sulfur,

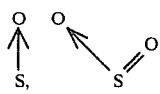

or $CH_2$;
Z is $-NHR_4$,

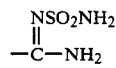

or $-CN$;
$R_1$ is $-NR_2R_3$,

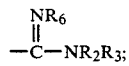

$R_2$ and $R_3$ are each independently H or alkyl, or both together with the nitrogen to which they are attached form a 5, 6 or 7-membered ring which may include one to three additional hetero atoms of N, O or S;
$R_4$ is selected from the group consisting of H, $$\begin{array}{ccc} \text{N}-\text{CN} & \text{CH}-\text{NO}_2 & \text{N}-\text{CN} \\ \parallel & \parallel & \parallel \\ -\text{C}-\text{NH}-\text{R}_5, & -\text{C}-\text{NH}-\text{R}_5, & -\text{C}-\text{S}-\text{R}_5, \end{array}$$

[thiadiazole structures with NH-R$_5$, N-N triazole with NHR$_5$, and pyrimidinone with alkaryl group]

$R_5$ is H or lower alkyl;
$R_6$ is H or lower alkyl or $R_6$ together with $R_2$ are ethylene or propylene and form a 5 or 6 membered ring with the nitrogen atoms to which they are attached;
or a pharmaceutically acceptable salt thereof.

Compounds within the scope of Formula I exhibit physiological activity in mammals including anti-secretory activity, histamine H$_2$-receptor antagonist activity, anti-ulcer activity and cytoprotective activity.

This invention also relates to methods for the treatment and prevention of gastrointestinal hyperacidity and ulcerogenic disorders in humans and other mammals comprising administering to a patient an effective amount of a compound within the description of Formula I.

DETAILED DESCRIPTION OF THE INVENTION

Preferred classes of compounds according to this invention are described by Formulae II, III, and IV:

[Formula II: naphthalene with (CH$_2$)$_d$—X—(CH$_2$)$_e$—Z and (CH$_2$)$_a$R$_1$ substituents]

or;

[Formula III: naphthalene with (CH$_2$)$_a$R$_1$ and (CH$_2$)$_d$—X—(CH$_2$)$_e$—Z substituents]

wherein:
a is 0, 1 or 2;
d is 0 or 1;
e is 2, 3 or 4;
X is oxygen or sulfur;
Z is —NHR$_4$ or $$\begin{array}{c} \text{NSO}_2\text{NH}_2 \\ \parallel \\ -\text{C}-\text{NH}_2 \end{array};$$

$R_1$ is —NR$_2$R$_3$;
$R_2$, $R_3$, $R_4$ and $R_5$ are as described above.

[Formula IV: naphthalene with (CH$_2$)$_d$—X—(CH$_2$)$_e$—Z and R$_1$ substituents]

wherein:
d is 0 or 1;
e is 2, 3 or 4;
X is oxygen or sulfur;
Z is —NHR$_4$ or $$\begin{array}{c} \text{NSO}_2\text{NH}_2 \\ \parallel \\ -\text{C}-\text{NH}_2 \end{array};$$

$R_1$ is —NR$_2$R$_3$;
$R_2$, $R_3$, $R_4$ and $R_5$ are as described above.

A most preferred class of compounds within the scope of Formula I comprises the compounds of Formula I wherein:
a is 0;
d is 0;
e is 3;
X is oxygen; and
Z is —NHR$_4$ or $$\begin{array}{c} \text{NSO}_2\text{NH}_2 \\ \parallel \\ -\text{C}-\text{NH}_2- \end{array}$$

A preferred subclass of compounds is described by Formula IV, wherein:
e is 3; and
X is oxygen.

Another preferred subclass of compounds is described by Formula IV, wherein:
d is 1;
e is 2; and
X is sulfur.

A most preferred class of compounds is described by Formula V.

[Formula V: naphthalene with (CH$_2$)$_d$—X—(CH$_2$)$_e$—NH—C(=N-triazolyl-CH$_3$)—NH$_2$ and R$_1$ substituents]

wherein:
d is 0 or 1;
e is 2, 3 or 4;
X is oxygen or sulfur;
$R_1$ is —NR$_2$R$_3$;
$R_2$ and $R_3$ together with the nitrogen to which they are attached form a 5, 6 or 7 membered heterocyclic ring which may include one to three additional hetero atoms of N, O or S;
or a pharmaceutically acceptable salt thereof.

A particularly interesting class of compounds according to Formula V comprises those compounds wherein R₁ is N-piperidyl, N-pyrrolidinyl, N-morpholinyl or N-azepinyl.

The compounds of Formulae I to V may also form hydrates and exhibit tautomerism. Formulae I to V are intended to encompass all hydrates and tautomers, as well as any diastereomers and optical enantiomers.

As employed above and throughout the disclosure, the following terms, unless otherwise indicated, shall be understood to have the following meanings:

"Lower alkyl" means an alkyl group as above, having 1 to about 4 carbon atoms. Examples of lower alkyl groups are methyl, ethyl, n-propyl, isopropyl, butyl, sec-butyl, and tert-butyl.

"5, 6 or 7 membered heterocyclic ring" means a nitrogen-containing ring of the formula —NY where Y is alkylene or alkylidinyl having from one to six carbon atoms, and may include one to three atoms of N, O or S. Exemplary heterocyclic groups include piperidyl, pyrrolidinyl, morpholinyl, azepinyl, pyrrolyl, imidazolyl, pyrazolyl, and thiamorpholinyl.

Representative examples of compounds of this invention are listed below in Tables A, B and C.

TABLE A

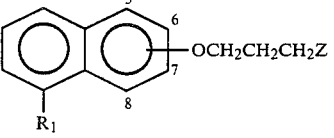

wherein substitution may by at the 5,6,7 or 8 position

| R₁ | Z |
|---|---|
| —N(CH₃)₂ | 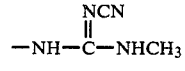 |
| 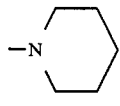 | 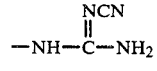 |
|  | 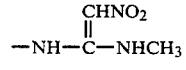 |
| —NH₂ | 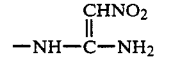 |
|  | 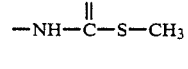 |
| 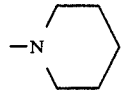 | 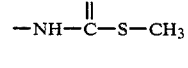 |
| 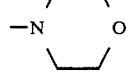 | 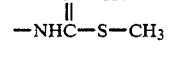 |
| —N(CH₃)₂ | 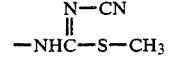 |

TABLE A-continued

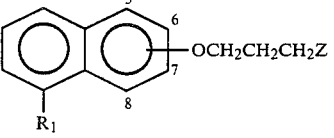

wherein substitution may by at the 5,6,7 or 8 position

| R₁ | Z |
|---|---|
| —NHCH₃ | 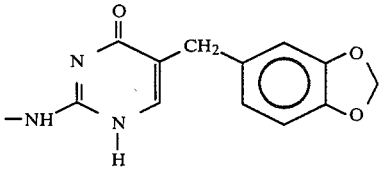 |
| 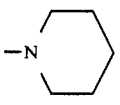 | 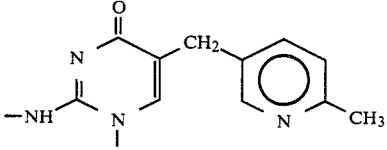 |
| 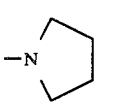 | 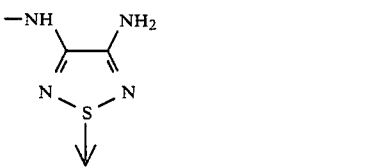 |
| —N(CH₃)₂ | 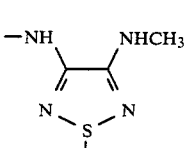 |
| —N(CH₃)₂ | 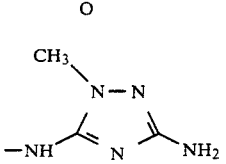 |
| 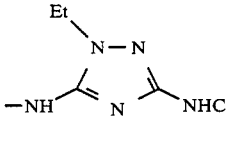 | 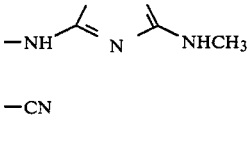 |
| 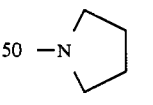 | 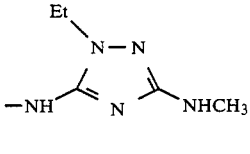 |
| 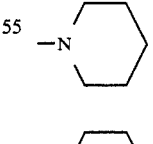 | —CN |
| 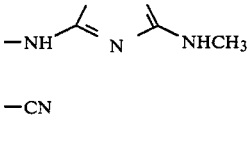 | 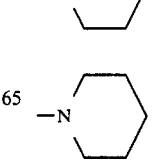 |

TABLE A-continued
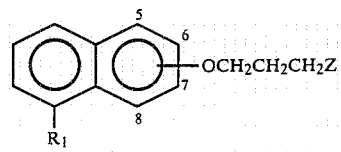
wherein substitution may by at the 5,6,7 or 8 position
| $R_1$ | Z |
|---|---|
| 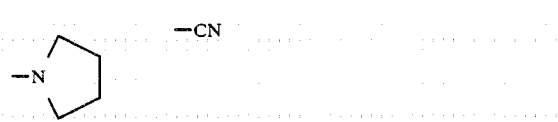 | |
| 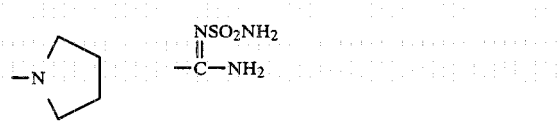 | |
| 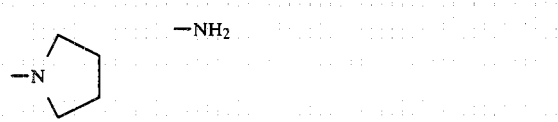 | |
| 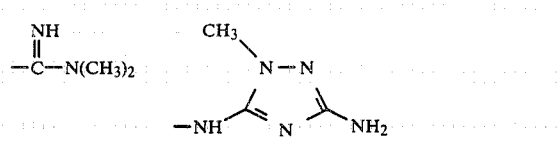 | |
| 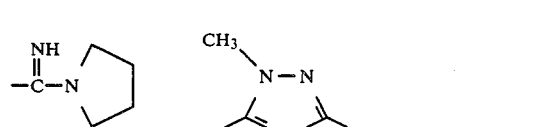 | |
| 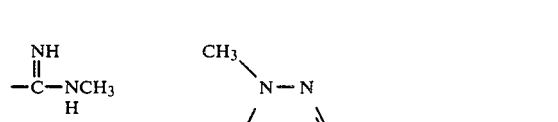 | |
| 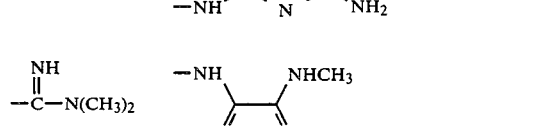 | |
| 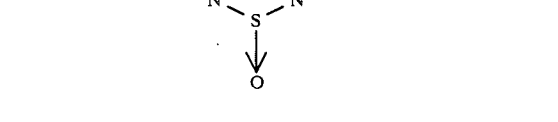 | |
| 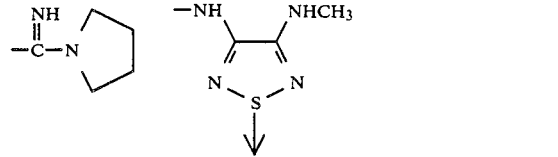 | |
TABLE A-continued
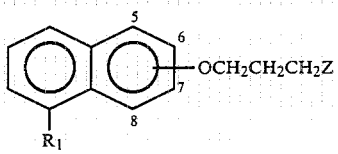
wherein substitution may by at the 5,6,7 or 8 position
| $R_1$ | Z |
|---|---|
| 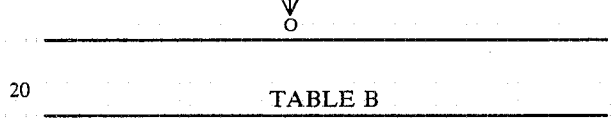 | |
TABLE B
| $R_1$ | Z |
|---|---|
| 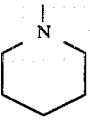 | |
| 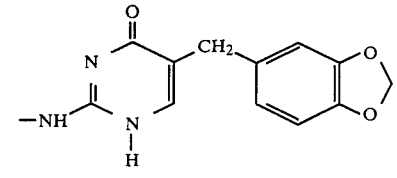 | |
| 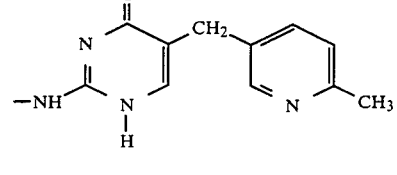 | |
| 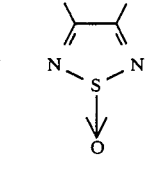 | |

TABLE B-continued

Structure: Naphthalene with R₁ and —OCH₂CH₂CH₂Z substituents

| R₁ | Z |
|---|---|
| —NHCH₃ | —NH-(4-amino-1,2,5-thiadiazole 1,1-dioxide), with NH₂ |
| —N(CH₃)₂ | —NH-(4-amino-1,2,5-thiadiazole 1,1-dioxide), with NH₂ |
| —N(CH₃)₂ | —NH-(4-methylamino-1,2,5-thiadiazole 1-oxide), with NHCH₃ |
| —N(CH₃)₂ | pyrimidinone with —NH— and CH₂-(6-methylpyridin-3-yl) |
| —N(Et)₂ | pyrimidinone with —NH— and CH₂-(1,3-benzodioxol-5-yl) |
| —N(Et)₂ | 1-methyl-1,2,4-triazole with —NH— and —NHCH₃ |
| —NHEt | —NH—C(=CHNO₂)—NH₂ |
| —NHCH₃ | —NH—C(=NCN)—SCH₃ |
| —N(piperidinyl) | —NH—C(=N—CN)—NHCH₃ |

TABLE C

Structure: Naphthalene with R₁ and —CH₂SCH₂CH₂Z substituents

| R₁ | Z |
|---|---|
| —N(piperidinyl) | —CN |
| —N(piperidinyl) | —C(=NSO₂NH₂)—NH₂ |
| —N(piperidinyl) | —NH₂ |
| —N(pyrrolidinyl) | —CN |
| —N(pyrrolidinyl) | —C(=NSO₂NH₂)—NH₂ |
| —N(pyrrolidinyl) | —NH₂ |

The compounds of this invention may be prepared by one of the following general synthetic schemes.

When the naphthalene ring is directly attached to the X component of Formula I, these compounds may be prepared from the naphthol (or naphthmercaptan) intermediate shown by Formula VI below. The appropriately substituted naphtholic (or mercaptyl) intermediate of Formula VI may be prepared by the reaction sequences illustrated in Scheme I.

The starting material may be a 1, 2, or 3-cyano or a 1, 2, or 3-nitronaphthol or naphthmercaptan, having the oxy or mercaptan substituent in the 5, 6, 7 or 8 position. These compounds can either be obtained from a commercially available source or prepared according to standard procedures known in the art.

The nitro compound may be converted in excellent yield to the amine by reduction using hydrazine in the presence of a catalyst such as palladium or charcoal.

The cyano compound may be converted to the amide by acid hydrolysis, treatment with a Lewis acid such as $BF_3$ in acetic acid, hydrogen peroxide in aqueous ethanolic sodium hydroxide solution, or by sodium hydroxide in DMSO. The resulting amide is either further reduced resulting in the methylene amine or subjected to a Hoffman or Curtius rearrangement to the corresponding amino compound. The rearrangement may be conducted by treatment of the amide with bromine and sodium methoxide in methanol followed by workup with calcium oxide and water.

The protecting group, $P_R$, may be methyl, benzyl or the N-phthalimido alkyl. If the protecting group is chosen to be other than the N-phthalimido alkyl, the protecting group is removed according to methods known in the art. If the protecting group is N-phthalimido alkyl, then it can remain on the synthetic intermediate preceding VI and used as in the subsequent reaction step.

The phenolic protecting group is then cleaved to obtain the intermediate of Formula VI.

as sodium methoxide, potassium t-butoxide or potassium carbonate. Ether coupling reagents other than a base and a bromide may also be used. (Scheme III)

Scheme III

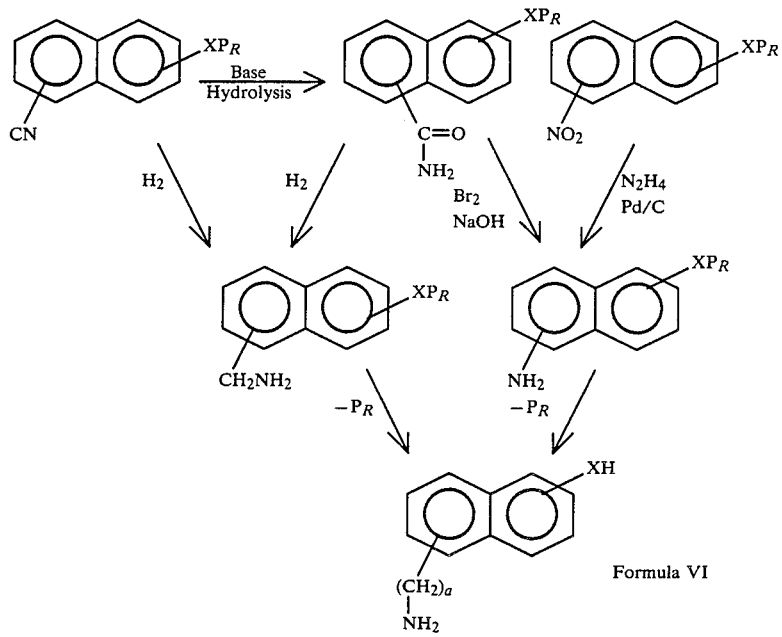

Formula VI

The starting material may also be the 1, 2, 3, or 4-carboxylic acid or ester thereof which may be converted to the amide by the condensation of the desired amine followed by reduction as shown in Scheme II.

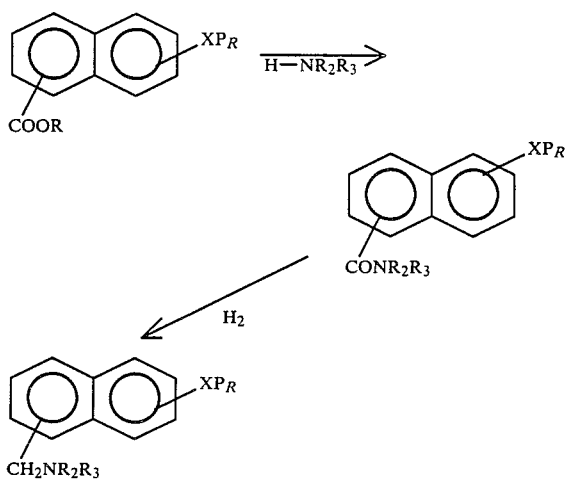

Scheme II

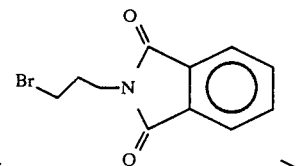

The formation of the ether linkage from VI is accomplished by treating the phenolic compound with a protected N-propylbromide in the presence of a base such The nitrogen protecting group is preferably phthalimido but can be any protecting group insensitive to the ether formation reaction conditions, such as a base insensitive group.

The amine compound is obtained by the removal of the protecting group, for example, the phthalimido group is removed with hydrazine hydrate. (Scheme IV)

Scheme IV

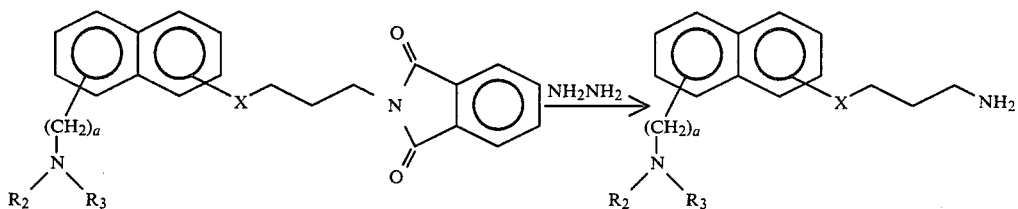

Scheme VI

The addition of the terminal $R_4$ group comprises treating the amine with an $R_4$ end group precursor unit including those groups listed in Scheme V below. The preparation of the precursors of the $R_4$ groups and the reaction conditions under which they are coupled to the primary amine are fully described in U.S. Pat. Nos. 4,104,381, 4,279,819, 4,323,566 and GB No. 2067987A, hereby incorporated by reference.

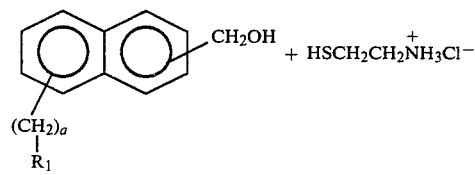

Scheme V

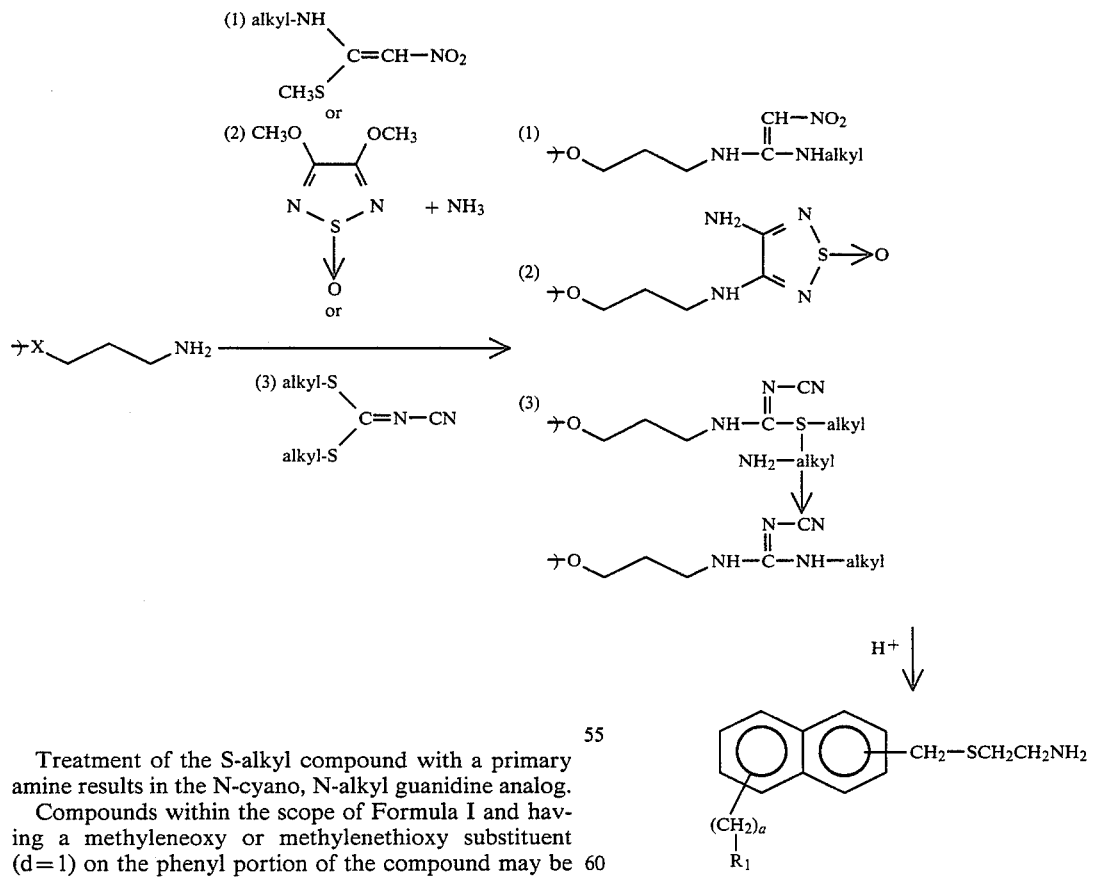

Treatment of the S-alkyl compound with a primary amine results in the N-cyano, N-alkyl guanidine analog.

Compounds within the scope of Formula I and having a methyleneoxy or methylenethioxy substituent (d=1) on the phenyl portion of the compound may be prepared by one of the reaction sequences described below.

The methyleneoxy or methylenethio ether may be prepared from the coupling of a 2-bromoethylene phthalimide in the presence of base or 2-thioethylamine, respectively, with the methylene hydroxy compound. Scheme VI illustrates the formation of the methylenethio ether.

Addition of the $R_4$ group may proceed as described above in Scheme V.

The methyleneoxy compound may be obtained by the reduction of a phenyl carboxylic acid or ester precursor such as Formula VII. The reduction may be accomplished by hydrogenation over a rhenium catalyst, by a hydride in the presence of a Lewis acid or by acidic electrolysis and depending on choice of conditions may take place before or after the formation of the amine.

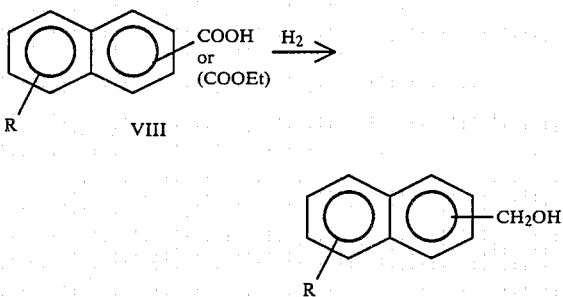

If the reduction to the methylene hydroxy compound occurs after the formation of the amine, the carboxylic acid intermediate is prepared analogously to the phenolic intermediate VI, with the acid being protected by its ester where appropriate.

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, malic acid, oxalic acid, succinic acid, glycolic acid, lactic acid, salicylic acid, benzoic acid, nicotinic acid, phthalic acid, stearic acid, oleic acid, abietic acid, etc.

The following are selected examples of the preparation of the compounds according to this invention.

EXAMPLE 1

The Preparation of
3-Amino-5-[3-[5-(1-Pyrrolidinylnaphthyloxy)]-Propylamino]-1-Methyl-1H-1,2,4-Triazole

Step 1. 1-Amino-5-methoxy naphthalene

Hydrazine hydrate (150 ml) is added slowly to a stirred mixture of 5-methoxy-1-nitro-naphthalene (320 g), and palladized charcoal (0.1 g) in 95% ethanol (2 liters) previously warmed to 50° C. When the hydrazine addition is complete, additional palladized charcoal (0.1 g) is added and the mixture heated to reflux for about one hour. The reaction mixture is filtered through Celite and the filtrate evaporated in vacuo resulting in a white solid which is recrystallized from $H_2O$ and ethanol.

Step 2. 5-Methoxy-1-pyrrolidinyl-naphthalene 1,4-Dibromobutane (220 g) is added dropwise to a stirred suspension of 1-amino-5-methoxynaphthalene (170 g) and sodium carbonate (200 g) in THF (300 ml), while maintaining the reaction temperature at less than 10° C. When the addition is complete, the stirred mixture is allowed to reach RT and refluxed overnight.

The reaction mixture is evaporated in vacuo, and the residue partitioned between ether and aqueous hydrochloric acid. The aqueous layer is made acidic (pH 5–6) by the addition of conc. HCl. The layers are separated and the ether layer washed with aqueous HCl. The aqueous extracts are combined and made basic with saturated sodium bicarbonate resulting in the formation of an immiscible oil. The oil is extracted with methylene chloride and the organic extract washed with saturated NaCl, dried over $Na_2SO_4$, filtered and evaporated in vacuo. The residual oil is used in the next step without further purification.

Step 3. 5-Hydroxy-1-pyrrolidinyl-naphthalene

5-Methoxy-1-pyrrolidinyl-naphthalene (90 g) is dissolved in glacial acetic acid (1 liter). 48% hydrobromic acid is added to the solution and the resulting reaction mixture heated to reflux for 3 hours. The reaction mixture is poured into water and crushed ice and the solution made alkaline to pH 8 to 9. The aqueous mixture is extracted with methylene chloride. The methylene chloride extract is back-extracted with 2% KOH solution and the combined basic layers made acidic by the addition of aqueous HCl. The addition is continued until a white precipitate appears. The aqueous solution is extracted with methylene chloride and the organic layer washed with $H_2O$, dried, filtered and evaporated in vacuo, yielding the desired product.

Step 4.
1-7-[3-(N-Phthalimido)propoxy]-1-pyrrolidinylnaphthalene

Potassium t-butoxide (6 g) is added to a stirred solution of 7-hydroxy-1-pyrrolidinyl-naphthalene (10 g) in dimethylformamide (100 ml). 26 g of N-(3-bromopropyl)phthalimide is added to the stirred reaction mixture and stirring is continued for about 24 hours. The reaction is partitioned between slightly basic $H_2O$ and diethyl ether. The layers are separated and the aqueous layer extracted with ether. The combined ether extracts are washed with 5% sodium hydroxide solution and $H_2O$. The ether extract is stirred with 5% aqueous hydrochloric acid solution, the layers separated and the ether extracted with additional aqueous 5% hydrochloric acid. The combined acidic aqueous layers are washed with ether and made strongly alkaline, resulting in an oily precipitate. The precipitate is extracted with diethyl ether which is washed with $H_2O$ and saturated sodium chloride solution dried and evaporated in vacuo, yielding the desired ether as a solid.

Step 5.
7-(3-Aminopropoxy)-1-pyrrolidinyl-naphthalene

85% hydrazine hydrate (9.6 ml) is added to a stirred solution of the phthalimido naphthalene prepared as described in the previous step (about 50 g) in absolute ethanol (about 500 ml). The reaction mixture is heated at reflux for about 3 hours and allowed to cool. The resulting precipitate is removed by filtration and washed with absolute ethanol. The filtrate is evaporated in vacuo and the residue triturated with 5% aqueous hydrochloric acid. The aqueous suspension is filtered and the solid washed with 5% hydrochloric acid. The filtrate is made strongly alkaline with 50% sodium hydroxide solution, resulting in an oily precipitate which is extracted into diethyl ether. The ether extract is washed with saturated sodium chloride solution, dried, filtered and the filtrate evaporated in vacuo, yielding the desired amine as an oil.

Step 6. 1-Cyano-3-[3-[7-(1-pyrrolidinyl naphthyloxy)]propyl]-2-methylpseudothiourea The amine from the preceding step (10 g) is dissolved in isopropanol (35 ml) and is added over a period of one minute to a stirred solution of S,S-dimethyl-N-cyanoiminodithiocarbonimidate (7 g) dissolved in 100 ml of isopropanol. The reaction mixture is stirred at RT overnight and evaporated in vacuo, yielding the desired cyano product as a viscous amber oil.

Step 7. 3-Amino-5-[3-[7-(1-pyrrolidinyl naphthyloxy)]propylamino]-1-methyl-1H-1,2,4-triazole Methyl hydrazine (11 ml) is added to a stirred solution of the cyanonaphthalene from the previous step (about 10 g) dissolved in dimethylformamide (110 ml). The reaction mixture is stirred at about 40° C. for 24 hours, and evaporated under vacuum resulting in a residue of amber oil. The oil is separated on a silica gel column (290 g; 70–230 mesh) using as eluent methanol in methylene chloride ranging from 10% methanol to 30% methanol. The major fractions are pooled and evaporated in vacuo, resulting in a viscous amber oil. The oil is triturated in anhydrous ether, resulting in the formation of the desired product as a solid which is filtered, washed with ether and dried. This solid is recrystallized from hot acetonitrile and dried under vacuum, resulting in a near-white powder.

EXAMPLE 2

The Preparation of N-[3-[5-(1-Diethylaminomethylene Naphthyloxy)]Propyl]-N'-Methyl-2-Nitro-1,1-Diaminoethane

Step 1. 1-Carbamoyl-5-methoxy-naphthalene

1-Cyano-5-Methoxy-naphthalene (36 g) is stirred with concentrated sulfuric acid (250 ml) and $H_2O$ (20 ml) on a steam bath for two hours and is allowed to cool. The reaction mixture is poured into a slurry of crushed ice and concentrated ammonium hydroxide (250 ml). The mixture is extracted with methylene chloride and the organic extract dried, filtered and evaporated, yielding the desired amide as a solid.

Step 2. 1-(N,N-Diethylcarbamoyl)-5-methoxy-naphthalene

1-Carbamoyl-5-methoxy-naphthalene (20 g) is suspended in 100 ml of 40% diethylamine hydrochloride in water and stirred under reflux overnight. The reaction mixture is evaporated in vacuo and the residue partitioned between 5% aqueous HCl and methylene chloride. The organic layer is separated, dried over $Na_2SO_4$, filtered and evaporated yielding the desired product as a white crystalline solid.

Step 3. 5-Methoxy-1-N,N-diethylaminomethylenenaphthalene

5-Methoxy-1-N,N-diethylcarbamoyl-naphthalene (25 g) dissolved in THF (100 ml) is added dropwise to a stirred mixture of lithium aluminum hydride (3.5 g) in THF (50 ml) while maintaining a gentle boiling under a nitrogen atmosphere. When the addition is complete, the reaction mixture is gently refluxed for two hours. The reaction mixture is allowed to cool and 3.5 ml of $H_2O$ added to the reaction mixture dropwise, followed by 3.5 ml of 15% sodium hydroxide solution and 10.5 ml of $H_2O$. The reaction mixture is filtered and the solid washed with methylene chloride. The filtrate is evaporated and the solid residue partitioned between methylene chloride and $H_2O$. The organic layer is separated, washed with saturated sodium chloride, dried over $NaSO_4$, filtered and evaporated, resulting in the desired product as a crystalline solid.

Step 4. 1-Diethylaminomethylene-5-hydroxy-naphthalene 15 g of 1-diethylaminomethylene-5-methoxy naphthalene obtained in the previous step are dissolved in glacial acetic acid (150 ml). 48% hydrobromic acid (150 ml) is added to the solution and the resulting reaction mixture heated to reflux for 3 hours. The reaction mixture is poured into $H_2O$ and crushed ice and the solution made alkaline to pH 8 to 9. The aqueous mixture is extracted with methylene chloride. The methylene chloride extract is back-extracted with 2% KOH solution and the combined basic layers made acidic by the addition of aqueous HCl. The addition is continued until a white precipitate appears. The aqueous solution is extracted with methylene chloride and the organic layer washed with $H_2O$, dried, filtered and evaporated in vacuo, yielding the desired product as an oil.

Step 5. 1-Diethylaminomethylene-5-[3-(N-phthalimido)-propoxy]-naphthalene

Potassium t-butoxide (6 g) is added to a stirred solution of 1-diethylaminomethylene-5-hydroxynaphthalene (10 g) in dimethylformamide (100 ml). 26 g of N-(3-bromopropyl) phthalimide is added to the stirred reaction mixture and stirred continued for about 24 hours. The reaction is partitioned between slightly basic $H_2O$ and diethyl ether. The layers are separated and the aqueous layer extracted with ether. The combined ether extracts are washed with 5% sodium hydroxide solution and $H_2O$. The ether extract is stirred with 5% aqueous hydrochloric acid solution, the layers separated and the ether extracted with additional aqueous 5% hydrochloric acid. The combined acidic aqueous layers are washed with ether and made strongly alkaline. The resulting oily precipitate is extracted with diethyl ether which is washed with $H_2O$ and saturated sodium chloride solution dried and evaporated in vacuo, yielding the desired ether as a solid.

Step 6. 5-(3-Aminopropoxy)-1-diethylaminomethylenenaphthalene

85% hydrazine hydrate (1 ml) is added to a stirred solution of the phthalimido naphthalene prepared as described in the previous step (about 5 g) in absolute ethanol (about 50 ml). The reaction mixture is heated at reflux for about 3 hours and allowed to cool. The precipitate is removed by filtration and washed with absolute ethanol. The filtrate is evaporated in vacuo and the residue triturated with 5% aqueous hydrochloric acid. The aqueous suspension is filtered and the solid washed with 5% hydrochloric acid. The filtrate is made strongly alkaline with 50% sodium hydroxide solution. The resulting oily precipitate is is extracted into diethyl ether. The ether extract is washed with saturated sodium chloride solution, dried, filtered and the filtrate evaporated in vacuo, yielding the desired amine as an oil.

Step 7.
N-[3-[5-(1-diethylaminomethylene-naphthyloxy)]-propyl]-N'-methyl-2-nitro-1,1-diaminoethene 1-Methylamino-1-methylthio-2-nitroethene (2 g) is added to a solution of the 1-diethylaminomethylenenaphthyloxy propylamine prepared in the preceding step (3 g) in absolute ethanol (30 ml). The reaction mixture is heated to reflux for about 2 hours while purging the reaction mixture with $N_2$. The mixture is allowed to cool and the resultant solid filtered, washed with diethyl ether and dried. The filtrate is evaporated in vacuo and the residue dissolved in hot absolute ethanol. Diethyl ether is added, resulting in the formation of a solid which is filtered and dried. The two solids are combined and dissolved in boiling isopropyl alcohol, allowed to cool, filtered, washed with isopropyl alcohol and ether, and dried under vacuum, resulting in the desired product as a white powder.

Various tests in animals may be carried out to show the ability of the compounds of this invention to exhibit pharmacological responses that can be correlated with activity in humans. These tests involve such factors as the effect of the compounds of Formula I on gastric secretion and their $H_2$ antagonist and cytoprotective activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compounds of the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

These tests are known to correlate well with gastric activity in humans and are standard tests used to determine anti-secretory properties.

The following tests determine the histamine $H_2$-receptor antagonist activity of the compound according to the present invention.

A. Isolated Guinea Pig Atria

The $H_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 111, *Molecular Pharmacology: The Mode of Action of Biologically Active Compound*. Vol. 1, Academic Press (1964).

1. Tissue Bath

A fifty ml jacketed tissue bath is maintained at 30° C. The bath consists of a Krebs-Henseleit buffer aerated with 95% $O_2$-5% $CO_2$, (pH 7.4). The buffer is prepared by mixing: 4 ml of an aqueous (distilled deionized) solution of $CaCl_2.2H_2O$ (0.37 g/ml); 4 ml of an aqueous (distilled deionized) solution of $MgSO_4.7H_2O$ (0.29 g/ml); 7.2 g of glucose; and, 2 liters of aqueous (distitlled deionized) solution containing NaCl (28 g), $NaHCO_2$ (8.4 g), KCl (1.4 g) and $KH_2PO_4$ (0.6 g).

2. Preparation of Atria

Male albino guinea pigs (400–700 g, preferably 500–600 g) are killed by a blow to the back of the head and exsanguinated by cutting jugular veins and carotid arteries. The thoracic skin is opened from this neck cut and the rib cage exposed. Both sides of the rib cage and diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taperpoint needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0M histamine (0.1, 0.3, 1.0, 3.0, etc.) In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agaonist and stimulates, then the dose is increased until the rate plateaus or the concentration is 1.0 mM. If, however, no agonistic activity is observed when the concentrations has reached 100M then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages ($\pm$SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the exophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH 10.0) is perfused and collected in 30 ml beakers. The beakers are changed every 10 or 15 minutes and the pH of these samples are recorded. Once the pH has stabilized around 6.5-7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225-231 (1979).

Male Sprague-Dawley rats 140-170 g are housed according to standard animal husbandry procedures. The rats are fasted twenty-four hours prior to testing. On the test day, rats are divided into groups of 5 or 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10× magnifying glass; the following scale is employed:

| Grade | Description |
|---|---|
| 0 | No lesions |
| 1 | 5 lesions, all <2 mm |
| 2 | 5 lesions, at least 1 > 2 mm |
| 3 | 5-10 lesions, all <2 mm |
| 4 | 5-10 lesions, at least 1 > 2 mm |
| 5 | 10 lesions, all <2 mm |
| 6 | 10 lesions, at least 1 > 2 mm |
| 7 | Perforation |

The average ulcer severity (±S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The cytoprotective effectiveness of the compounds of Formula I is evaluated according to the following test procedure.

Male Sprague-Dawley rats 150-200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2N NaOH (1 ml) or 0.6N HCl (1 ml), regardless of body weight. One hour after administration animals are sacrificed by cervical dislocation, their stomachs are removed, opened along the greater curvature, rinsed under running tap water and examined for lesions with a 2×-10× magnifying glass.

The reduction of lesion count, lesion severity score and ulcer index as compared to similar measurements made in the controls was expressed as a percentage. Measurement of statistical significance of the results was done by standard methods.

The average ulcer severity (±S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The compounds of the present invention that exhibit anti-secretory, anti-ulcer, $H_2$-antagonist and cytoprotective activity are useful in the treatment of gastrointestinal ulcerogenic disorders in mammals, including humans. These compounds both aid in the healing of such ulcers and also prevent their formation.

In particular, the compounds according to Formulae I to VI are useful: in the treatment and prevention of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, $H_1$-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day.

We claim:

1. A compound of the formula

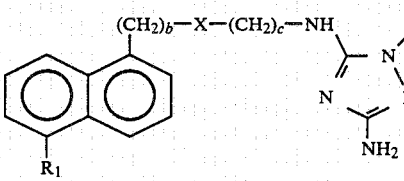

wherein:
b is 0 or 1;
c is 2, 3, or 4;
X is oxygen or sulfur;
$R_1$ is $-NR_2R_3$;
$R_2$ and $R_3$ together with the nitrogen to which they are attached form a heterocyclic ring of the formula $-N(CH_2)_d$, where d is 4, 5 or 6, morpholinyl, pyrrolyl, imidazolyl, pyrazolyl or thiamorpholinyl; or a pharmaceutically acceptable salt thereof.

2. A method for decreasing acid secretion in the gastrointestinal tract of mammals by administering thereto an anti-secretory effective amount of a compound according to claim 1.

3. A method for the treatment of gastrointestinal hyperacidity and ulceration in a mammal comprising administering thereto an effective amount of a compound according to claim 1.

4. A method for enhancing the gastrointestinal resistance to gastrointestinal irritants in humans and mammals comprising administering thereto an effective cytoprotective amount of a compound of the formula according to claim 1.

5. A pharmaceutical composition wherein the active ingredient is an effective $H_2$-antagonist amount of a compound according to claim 1 in admixture with a pharmaceutical carrier.

* * * * *